United States Patent [19]

Duggins

[11] Patent Number: 4,729,829
[45] Date of Patent: Mar. 8, 1988

[54] HOLLOW FIBER PLASMAPHERESIS MODULE

[75] Inventor: Ray B. Duggins, Chadds Ford, Pa.

[73] Assignee: E. I. Du Pont de Nemours and Company, Wilmington, Del.

[21] Appl. No.: 930,093

[22] Filed: Nov. 13, 1986

Related U.S. Application Data

[60] Continuation of Ser. No. 690,092, Jan. 9, 1985, abandoned, which is a division of Ser. No. 450,221, Dec. 16, 1982, Pat. No. 4,668,399, which is a continuation-in-part of Ser. No. 349,371, Feb. 16, 1982, abandoned, which is a continuation-in-part of Ser. No. 287,116, Jul. 22, 1981, abandoned.

[51] Int. Cl.$^4$ .............................................. B01D 13/01
[52] U.S. Cl. ........................... 210/195.2; 210/433.2; 210/321.8; 210/321.72
[58] Field of Search ............... 210/195.2, 257.2, 321.1, 210/323.2, 433.2

[56] References Cited

U.S. PATENT DOCUMENTS

| | | | |
|---|---|---|---|
| 3,342,729 | 9/1967 | Strand | 210/654 X |
| 4,176,156 | 11/1979 | Asanuma et al. | 422/25 |
| 4,191,182 | 3/1980 | Popovich et al. | 210/433.2 X |
| 4,247,498 | 1/1981 | Castro | 264/41 |
| 4,343,705 | 8/1982 | Legg | 210/637 |

OTHER PUBLICATIONS

Gurland, H. J. et al., "Clinical Applications of Macromolecular . . . "; T.A.S.A.I.O., 5/1981 (vol. 27), pp. 356–363.

Primary Examiner—David Sadowski

[57] ABSTRACT

Hollow fiber plasmapheresis module and process, said module comprising hollow fibers having cell-retaining pores and an effective length (L) to lumen diameter (D) ratio L/D not greater than 16,400 cm$^{-1}$ D (L and D being in centimeters) within a housing having a blood inlet for conducting blood to the fibers, an outlet for conducting exit (plasma-depleted) blood from the fibers, and a plasma outlet for conducting plasma out of the module.

7 Claims, 5 Drawing Figures

PLASMAPHERESIS APPARATUS

Fig. 1 PLASMAPHERESIS APPARATUS

Fig. 2 RECYCLE FLOW

Fig. 3 — FORWARD STROKE

Fig. 4 — REVERSE STROKE

HOLLOW FIBER PLASMAPHERESIS MODULE

CROSS-REFERENCE TO RELATED APPLICATIONS

This is a continuation of application Ser. No. 690,092 filed Jan. 9, 1985 (now abandoned) as a division of application Ser. No. 450,221 filed Dec. 16, 1982, now U.S. Pat. No. 4,668,399, which is a continuation-in-part of application Ser. No. 349,371 filed Feb. 16, 1982 as a continuation-in-part of application Ser. No. 287,116 filed July 22, 1981, the last two-mentioned applications now abandoned in favor of continuation-in-part application Ser. No. 478,812 filed Mar. 30, 1983.

TECHNICAL FIELD

This invention relates to plasmapheresis using microporous hollow fibers.

BACKGROUND INFORMATION

Plasmapheresis is a process of separating plasma from whole blood. The plasma-depleted blood is comprised principally of cellular components, e.g., red blood cells, white blood cells and platelets. Plasma is comprised largely of water, but also contains proteins and various other non-cellular compounds, both organic and inorganic.

Plasmapheresis is currently used to obtain plasma for various transfusion needs, e.g., preparation of fresh-frozen plasma for subsequent fractionation to obtain specific proteins such as serum albumin, to produce cell culture media, and for disease therapies involving either the replacement of plasma or removal of specific disease contributing factors from the plasma.

Plasmapheresis can be carried out by centrifugation or microfiltration. Microfiltration apparatus generally utilize microporous membranes. The pores are cell-retaining pores, that is, the pores substantially retain cellular components but allow plasma to pass through. Typically, cell-retaining pores are of substantially uniform diameter and are of a size within the range 0.1 to 1.0 micrometer, that is, between membranes the pore size is within this range, but in any single membrane the pores are of substantially the same size.

Various planar membrane devices are disclosed in the literature. These include various configurations of membranes and flow paths. In general, microporous hollow fibers are being increasingly used. Gurland et al., in a paper presented at the 1981 annual meeting of the American Society for Artificial Internal Organs, reported that three hollow fiber plasmapheresis modules were commercially available. These are the Plasmaflo 01, Plasmaflo 02 and Plasmaflux, the first two utilizing cellulose diacetate membranes with a maximum pore size of 0.2 $\mu$m, and the third, utilizing polypropylene with a maximum pore size of 0.5 $\mu$m. Other features are listed below.

| Module | Lumen (inner diameter) ($\mu$m) | Effective length (cm) | Effective surface (M$^2$) | Wall thickness ($\mu$m) |
|---|---|---|---|---|
| Plasmaflo 01 | 370 | about 20 | 0.65 | 160 |
| Plasmaflo 02 | 330 | about 20 | 0.5 | 60 |
| Plasmaflux | 330 | about 20 | 0.5 | 140 |

"Continuous plasmapheresis", as the term is used herein, is the process of continuously separating plasma from whole blood. Thus, as the term is used herein, "continuous plasmapheresis", and the apparatus needed to carry out a continuous plasmapheresis, must be able to provide, from whole blood, sufficient plasma, for example, at least about 500 mL, in a relatively short time, for example, 15 minutes to 3 hours, without substantial fouling of the membrane pores. The whole blood used in this invention either can be provided directly by a donor or patient or it can first be collected from a donor or patient and subsequently introduced into the apparatus of this invention, for example, from a reservoir.

It is an object of this invention to provide a hollow fiber plasmapheresis module which provides a high rate of plasma collection per unit area of membrane and which thus requires a small extracorporeal blood volume and a small surface area of membrane material, considered a foreign material to the blood. Another object is to provide such a module which not only provides a high plasma flux but also a high hematocrit in the plasma-depleted fraction. A further object is to provide a module which can operate continuously for longer periods of time than conventional plasmapheresis modules, thus making it suitable for use in continuous plasmapheresis. Another object is to provide such a module which is easy to assemble and easy to use without making extensive adjustments. A further object is to provide a plasmapheresis process employing hollow fiber membranes. Other objects will become apparent hereinafter.

BRIEF DESCRIPTION OF THE DRAWINGS

FIG. is a flow diagram which shows the hollow fiber module of the invention as it may be used with attendant communicating apparatus in carrying out a continuous plasmapheresis in either the steady state/recycle or pulsed flow mode of the invention.

SUMMARY OF THE INVENTION

Figure 1:
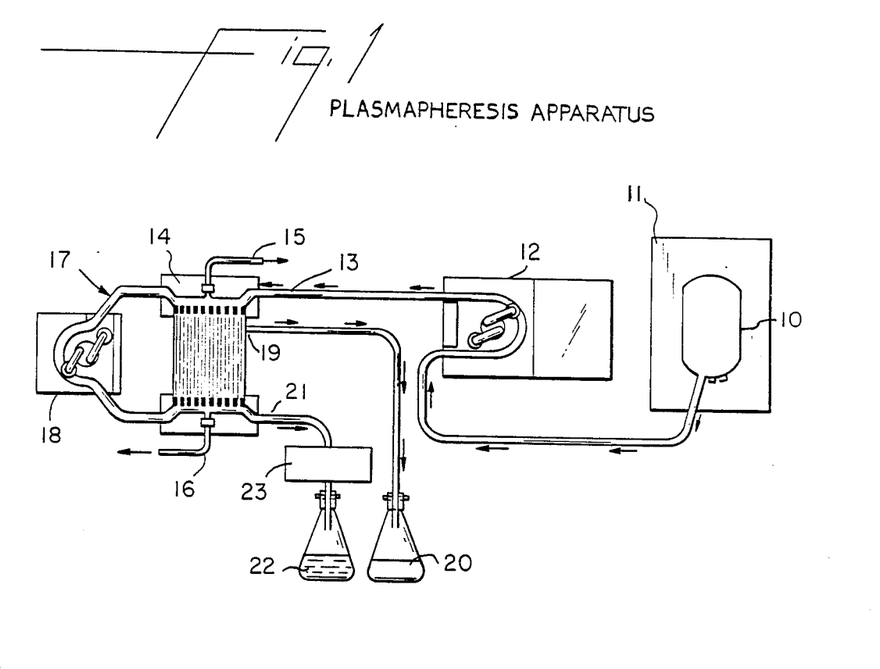

In my earlier applications, supra, are disclosed and claimed process and apparatus for carrying out plasmapheresis using reciprocatory pulsatile blood flow across a porous membrane, such as a flat membrane or hollow fibers. The instant invention involves the use of hollow fibers but, unlike the earlier invention, the flow of blood across the membrane can be either of the reciprocatory pulsatile type or of the steady state type. The steady state type invention also includes a variation wherein a recycle blood flow is employed. FIG. 1 depicts an apparatus for carrying out either the steady state/recycle or pulsed flow mode of the invention. FIG. 1 depicts a plasmapheresis apparatus consisting of a whole blood reservoir 10 in a constant temperature bath 11, a supply pump 12 which conveys the whole blood from the reservoir 10 to the blood inlet 13 of the hollow fiber membrane module 14, 15 to inlet of pressure transducer and 16 to outlet of pressure transducer, tubing loop 17 and pump 18 for use in the recycle and pulsed flow modes of the invention, plasma outlet 19 for removal of plasma 20, plasma-depleted blood outlet 21 for removal of the plasma-depleted blood 22, and back pressure valve/pump 23 between outlet 21 and the plasma-depleted blood 22. Such an apparatus without the left pump 18 and recycle loop 17 can be used to carry out the steady state mode of the invention.

The invention herein resides in a hollow fiber plasmapheresis module comprising hollow fibers having cell-retaining pores and an effective length substantially less than that commonly used in the art, within a housing having a blood inlet for conducting blood to the fibers, an outlet for conducting exit (plasma-depleted) blood from the fibers, and a plasma outlet for conducting plasma out of the module. The invention also resides in a process for using the aforesaid module for carrying out a plasmapheresis, especially on a continuous basis on a human subject. The immediately-following discussion is directed to the mechanics of steady state, recycle and reciprocatory pulsatile flow (pulsed flow) embodiments of the invention. Variables with each flow mode and their relationship to module performance are also discussed.

STEADY STATE FLOW PLASMAPHERESIS

The most desirable microporous hollow fiber plasmapheresis device removes the largest amount of plasma in the least amount of time, given the limited blood flow rate available from the patient. In this type of unit operating in the steady state flow mode, whole blood is pumped to one end of the fibers. As the blood flows through the fibers some of the plasma escapes through the pores, leaving blood at the outlet with a slightly elevated hematocrit. An adjustable clamp, valve or pump 23 can be placed on the blood outlet line to maintain the desired level of pressure within the module.

A problem with steady state flow is the interrelationship of outlet hematocrit and the quantity of plasma produced. Time is necessary for the plasma to be forced out through the pores. Faster blood flow rates allow more plasma to be produced, but a larger volume of whole blood is needed. The net result is that the hematocrit is lower than is obtained with slower blood flow rates. The optimum operating conditions thus depend on the goals set for the particular module. High hematocrit goals dictate a lower optimum blood flow rate, whereas peak plasma production requires faster blood flow rates. Under steady state flow conditions the best mode represents a compromise of these parameters.

RECYCLE FLOW

Figure 2:
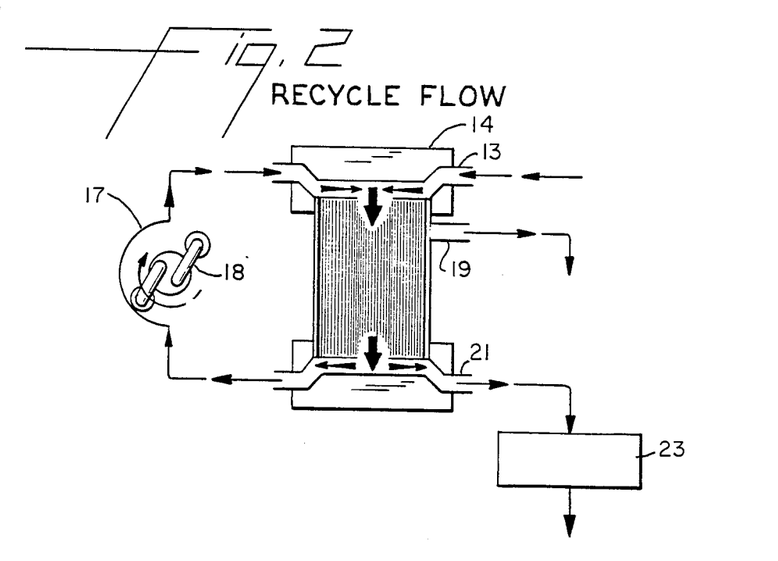
FIG. 2 is an enlarged view of a part of FIG. 1 to show the direction of blood flow in the recycle mode of the invention.

A variation of the steady state mode is the recycle flow mode wherein the flow of whole blood is augmented with some of the higher hematocrit blood that exists the fibers. A tubing loop 17 and a pump 18 are added to the device to recycle the higher hematocrit blood. This is shown in FIGS. 1 and 2. FIG. 2 depicts the flow of blood in the tubing loop 17 as going in a direction from the region of the module outlet to the region of the module inlet. It is to be understood that the recycle pump 18 can also be installed so that the flow of blood in the tubing loop goes in the reverse direction. In the recycle mode, the velocity of blood flowing through the module is increased, which in turn enhances plasma production. This result is achieved without increasing the flow rate of the blood, for example, from the patient. The hematocrit of the incoming blood thus is increased before it enters the fibers due to the mixing of the inlet blood supply and the blood in the recycle loop which has already been filtered. By utilizing the recycle flow mode a higher hematocrit and increased plasma production, as compared to steady state flow, can be realized. However, under this mode of operation the hematocrit and plasma production decrease with increasing time of operation. The cause of this deterioration of results is related to blockage of the membrane pores by the blood cells, as will be described below.

It is generally recognized in the art that the rate of plasma flow through the pores of the fiber (flux density) is usually not dependent on the transmembrane pressure (TMP) as long as the TMP is within certain limits (the "plateau region"). Below about 50 mm of Hg pressure plasma flow rises sharply with increasing pressure, as it does above about 175 mm of Hg pressure; above about 175 mm of Hg, however, there is grave risk of hemolysis. For a recycle flow plasmapheresis unit to be economically and medically acceptable, it should be operated in this "plateau region".

Classical fluid mechanics equations can be written to demonstrate that the transmembrane pressure varies along the length of the fiber. Initially, plasma production is greatest in the area of the fiber membrane near the whole blood inlet (the upper end of the fibers) where the transmembrane pressure is in the plateau region. This pressure drops along the length of the fiber, falling to 0 mm of Hg, and then below 0 (with packed cell pumping), near the outlet (the lower end of the fibers) for the plasma-depleted blood (also referred to herein as "packed cells", "filtered blood" and "cellular-enriched blood"). This negative TMP draws some of the plasma that was forced through the pores along the upper end of the fibers back through the pores along the lower end of the fibers, resulting in a decrease in net plasma production. Thus, the long term performance of a plasmapheresis unit operated in the recycle flow mode can be subject to the adverse effects of negative TMP.

In addition, the long term performance of the recycle mode is deficient due to another factor. As the module operation continues, some cellular components of the blood are drawn to the fiber pores with the plasma flow and block the pores, preventing further plasma flow through the pores. This pore blockage begins in the region of the fiber that experiences the highest transmembrane pressure, generally the region closest to the whole blood inlet. As the pores in this region become blocked, plasma flows through the next available open pores, in which event additional pore blockage takes place. Pore blockage continues down the fiber until all the pores are blocked.

Pore blockage may be diminished, either by decreasing the inlet blood flow or by decreasing the transmembrane pressure. Either method undesirably reduces the plasma output and increases the time necessary for carrying out the plasmapheresis.

RECIPROCATORY PULSATILE FLOW

In this mode, also referred to as pulsed flow, the advantage of recycle flow, that is, increased blood velocity through the fibers, is retained, while the problem of cellular deposition in the pores is diminished.

Figure 3:
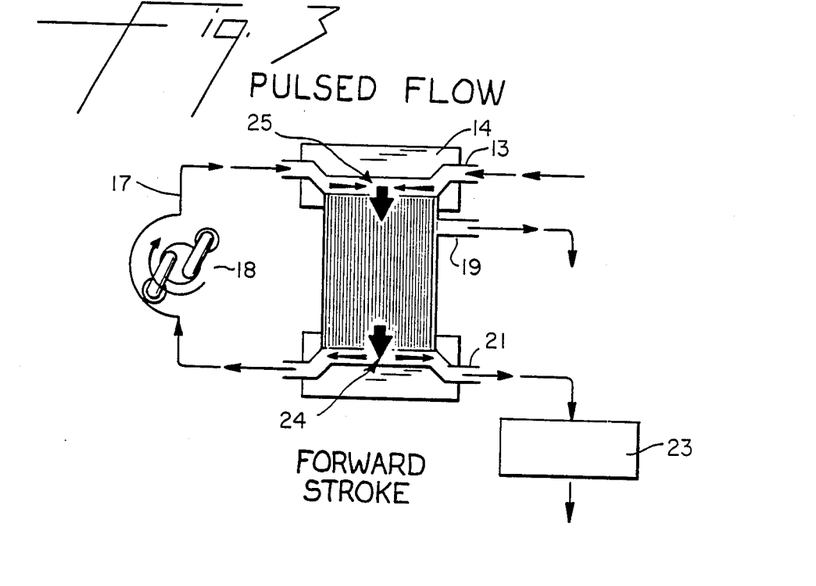
FIG. 3 shows the direction of blood flow on the forward stroke of the pulser pump in the pulsed flow mode of the invention.
Figure 4:
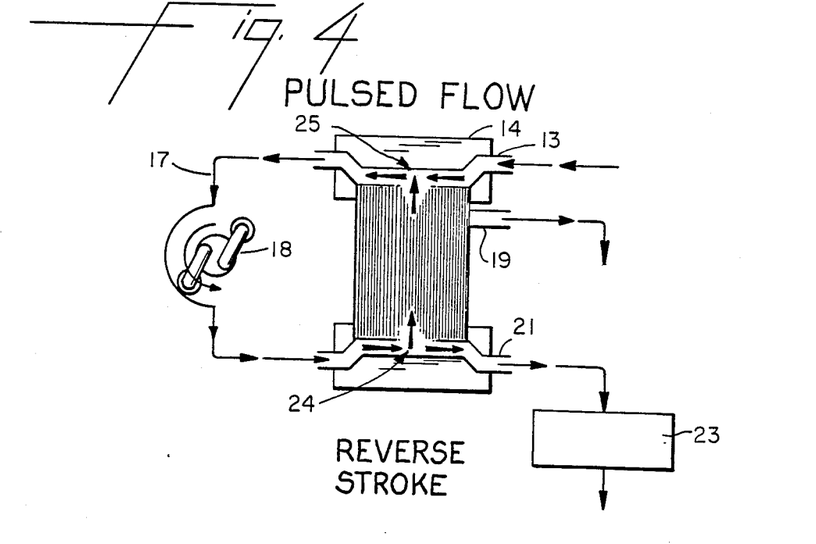
FIG. 4 shows the direction of blood flow on the reverse stroke in this mode of operation.

To operate in the pulsed flow mode, a tubing loop 17 is included in the plasmapheresis unit to connect the two ends of the module 14, as shown in FIGS. 1, 3 and 4. This loop includes a pulser pump 18 which periodically reverses direction at a preselected frequency. The pump alternately draws blood from the exit (efferent) end 24 of the unit and pumps it into the whole blood inlet (afferent) end 25 of the unit on a forward stroke (FIG. 3), then reverses direction and draws blood from the afferent end 25 of the module and pumps it into the efferent end 24 on a reverse stroke (FIG. 4). Along with the frequency, the length and/or velocity of each stroke can be set, these variables being useful in controlling the volume of blood passing through the loop. The volumes of blood passing through the loop on the forward and reverse strokes need not be the same, and preferably are not the same. The volume of blood being pulsed in the system on the either stroke is at least 5%, preferably at least 10%, of the total volume of blood in the system.

On the forward stroke (FIG. 3) when the inlet whole blood and the filtered (higher hematocrit) blood meet at the afferent end 25 of the module, they are forced through the fibers under an increased pressure. At the efferent end 24 of the module the blood is under less pressure and, in fact, this decreased pressure may, for example, as described hereinafter for a preferred embodiment, result in a partial vacuum.

When the direction of the pulser pump is reversed (FIG. 4), blood from the blood supply and from the module flows to the pulser loop 17 and a partial vacuum may result at the afferent end 25 of the module. Vacuum formation can be controlled by proper adjustment of a back pressure valve/pump 23 on the filtered blood outlet line from outlet 21. This valve, properly adjusted, is also useful in optimizing vacuum formation of the forward pump stroke. The blood exiting the pulser loop at the efferent end 24 of the module can either flow up through the module or out through the filtered blood outlet 21. The net result is a smaller total flow through the module during the reverse stroke. Thus, the afferent end 25 of the module and the forward stroke are the most efficient parts of the plasmapheresis unit for this mode of operation, and for this reason, it is preferred that the volume of liquid from the pulser loop be greater on the forward stroke than on the reverse stroke.

Figure 5:
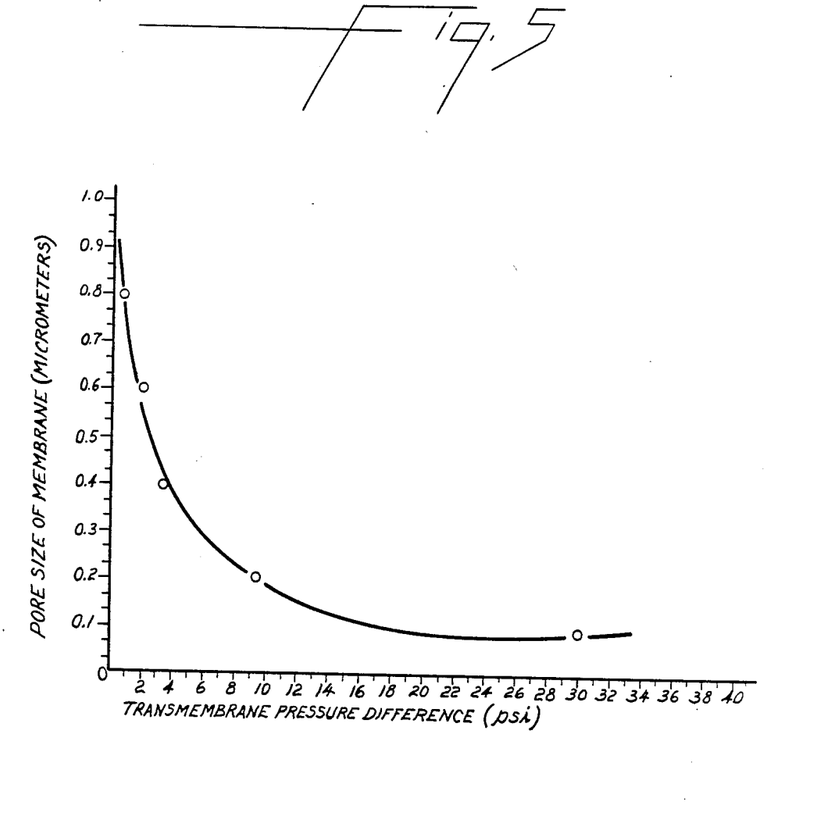
FIG. 5 shows the variation of transmembrane pressure difference with variation of membranes pore size; thus a higher transmembrane pressure difference can be tolerated as the pore size is decreased.

Further regarding the operation of the pulser pump on the forward stroke, the liquid required to fill the pulser loop can come from three sources: (1) the filtered blood exit line, (2) the filtered blood just exiting the fibers, and (3) back flow of plasma through the fiber pores. The amount provided by each source depends on the relative resistances to flow. During normal operation the aforesaid back pressure valve is closed far enough to maintain a peak transmembrane pressure of 75-130 mm of Hg at the afferent end 25 of the module; consequently, back flow from the filtered blood exit line will be minimal. Ideally, the pulser loop 17 should be filled mostly with filtered blood exiting the fibers, with only a minimum back flow of plasma, to maintain clean pores but not seriously diminish the output of plasma. This desired balance can be achieved in part by adjusting the ratio of effective fiber length to lumen diameter (L/D ratio). Using too high an L/D ratio may lead to an undesirable reduction in the flow of filtered blood from the fibers, thus diminishing plasma production. High L/D ratios are also undesirable because the resistance to blood flow is so great that unacceptably high pressures may be necessary to maintain flow; the high pressure may cause hemolysis. See FIG. 5 which shows the relationship of polycarbonate membrane pore size to transmembrane pressure difference at initial appearance of plasma hemolysis (>10 mg/dl).

As indicated above, the reversible pulser pump 18 can be adapted to vary any or all of: the frequency of stroke, the length of the stroke, the velocity of the stroke. In a preferred embodiment the pulser pump is operated so that the volume of liquid passing through the loop on the forward stroke of the pump is greater than the volume of liquid going through the loop on the reverse stroke.

The aforesaid discussion presumes that the whole blood inlet and the plasma-depleted blood outlet of the module are used as such during the entire plasmapheresis carried out therein. It is to be understood, however, that this need not be, since the module can be operated in a cyclic fashion such that the functions of the inlet and outlet are periodically reversed.

GENERAL DISCUSSION

The module for carrying out a plasmapheresis in accordance with any of the aforesaid three modes of operation may be described as an improved microfiltration module for separating whole blood into a cellular-enriched fraction and a plasma-enriched fraction, the module comprising in combination a plurality of porous, blood wettable hollow fibers having pores capable of passing plasma but not cellular components, the fibers being further characterized in that the pore size is within the range 0.1 to 1.0 μm, preferably 0.4 to 0.6 μm, and the lumen diameter (D) is no more than 0.050 cm, preferably D is 0.015 to 0.050 cm, the fibers being of substantially equal lengths and terminating in first open ends and second open ends; a liquid tight housing to contain the fibers; liquid tight sealing means cooperating with the housing and the first open ends of the fibers; liquid tight sealing means cooperating with the housing and the second open ends of the fibers, the two sealing means dividing the housing into two end chambers and one central chamber, the end chambers being in liquid transfer relationship with each other through the hollow fibers; blood inlet means for introducing whole blood into one end chamber; blood outlet means for removing a cellular-enriched (plasma-depleted) blood fraction from the other end chamber; and plasma outlet means for removing a plasma-enriched blood fraction from the central chamber, the improvement characterized in that the effective length (L) of each fiber is not greater than 16,400 cm$^{-1}$ D$^2$, that is, the L/D ratio is no greater than 16,400 cm$^{-1}$ D (L and D being in centimeters). "Effective length" is defined as that portion of the fiber, between the ends, through which plasma passes. Excluded from the effective length, therefore, are those portions of the fibers, at the ends, embedded in the sealing means, for example, a potting resin. It is to be understood regarding the aforesaid ranges of membrane pore size that the porous membrane fibers used herein have pores which are substantially uniform in size and that the substantially uniform size must be within the recited ranges.

At D=0.033 cm with the aforesaid L/D ratio, in carrying out the pulsed flow mode of the invention, it has been found that the use of hollow fibers having an L/D ratio of not greater than about 540, and especially those having an L/D ratio of about 100 to about 350, can provide high plasma flux, that is, rate of plasma collection (Qp), with high outlet hematocrit (hct), that is, volume percent of red blood cells in the plasma-depleted blood which is collected. In the steady state mode of the invention, the L/D ratio should not be greater than about 300, preferably about 100 to about 300. In the recycle mode of the invention, the L/D ratio should not be greater than about 460, preferably about 100 to about 350. In general, the lower the L/D ratio within the aforesaid ranges the more satisfactory are the results achieved. The rate of collection of plasma-depleted (exit) blood is referred to hereafter as $Q_{pc}$. High plasma flux is advantageous because it permits carrying out a plasmapheresis with a small extracorporeal blood volume. It is also advantageous because it permits carrying out such treatment while exposing the blood to a minimum area of fiber membrane and associated apparatus (foreign substances to the blood).

The fibers should be wettable by the blood and are preferably hydrophilic. The walls should be thin since permeability generally increases as wall thickness decreases.

The hollow fibers can be comprised of materials commonly available for such use, that is, materials which are or can be made biocompatible, permeable and blood wettable. These include, particularly, polymeric materials such as polyesters, polyamides, polycarbonates, polysulfones, methacrylate polymers, acrylonitrile polymers, and polypropylene which has been suitably treated to achieve the requisite wettability. Such hollow fibers can be prepared by known techniques. These include, for example, the techniques disclosed by Gerlach et al., British Specification No. 2,026,381A.

The module, which comprises fibers, potted in a resin, within a housing, can also be prepared by known techniques. The housing, which can be of any convenient shape, for example, cylindrical, should be made from a blood-compatible material, such as poly(methyl methacrylate). A blood inlet port is located near one end of the housing, for conducting whole blood into the hollow fibers, and an outlet port, for collecting plasma-depleted (cellular-enriched) blood, is located near the other end. A third port, a plasma outlet port, is used for collection of plasma which passes through the walls of the fibers. The module provides high plasma flux and high outlet hematocrit with small extracorporeal blood volume and small fiber membrane surface area.

Preferably, the module includes means for conducting the blood through the fibers in reciprocating pulsatile flow (pulsed flow), as described in my earlier applications and hereinabove. Such means include, for example, a blood circulating loop between an inlet and an outlet, there being an oscillator located on the loop. The inlet and outlet for connection to the oscillator can be the same as or different than the inlet and outlet used for feeding blood and collecting plasma-depleted blood, respectively.

The use of hollow fibers in this invention provides numerous advantages over the use of flat membranes. Some advantages are: the use of hollow fibers provides a large amount of membrane area in a small volume of space; the hollow fibers do not require membrane plasma drainplates; hollow fibers provide an excellent geometric configuration for achieving a uniform flow across the membrane; hollow fibers can be produced economically, as can the housing for the fibers; and no restraining clamps or heavy casings are required for hollow fiber housings. Conveniently, the module containing hollow fibers can be purged of air, filled with saline and stored ready-for-use using techniques routinely used with hemodialysis modules. Still another advantage of the hollow fiber module of this invention is that it is reusable, at least once, particularly in the pulsed flow mode of operation. For example, the wettable polypropylene fibers used in the examples hereinafter were cleaned readily using dilute aqueous sodium hypochlorite.

The pulsed flow mode of the invention is superior to both steady state and recycle flows because it removes more plasma per unit area of membrane in a shorter period of time. In addition, the unit can operate continuously for a longer time than the other modes. Moreover, using the pulsed flow system provides several attractive advantages to both the user and the manufacturer. A small unit with fewer fibers can outperform the presently available steady state flow units. The user also benefits from shorter treatment time, smaller extracorporeal volume of blood needed, reduced exposure of the blood to foreign surfaces and reduced module cost.

The steady state mode of the invention can be described as an improved method for plasmapheresis carried out in a system with a plurality of blood wettable porous membrane hollow fibers having open inlet end and open outlet ends, each fiber having a lumen diameter (D) of no greater than 0.050 cm, preferably 0.015 to 0.050 cm, the pore size of the porous membrane being within the range 0.1 to 1.0 $\mu$m, preferably 0.4 to 0.6 $\mu$m, the improved method comprising:

(a) conducting blood in a forward direction into and through the fibers while maintaining a mean positive transmembrane pressure difference across the membranes from inlets to outlets of the hollow fibers;

(b) collecting plasma-depleted blood from the outlets of the hollow fibers; and (c) collecting plasma which has passed through the pores of the membranes, the effective length of the hollow fibers being such that the L/D ratio is no greater than 16,400 cm$^{-1}$ D (L and D being in centimeters) and the velocity of the blood in step (a) being such that the shear rate is 50 to 2500 sec$^{-1}$, preferably 90 to 100 sec$^{-1}$.

The recycle mode of the invention can described as an improved method for plasmapheresis carried out in a system with a plurality of blood wettable porous membrane hollow fibers having open inlet ends and open outlet ends, each fiber having a lumen diameter (D) of no greater than 0.050 cm, preferably 0.015 to 0.050 cm, the pore size of the porous membrane being within the range 0.1 to 1.0 $\mu$m, preferably 0.4 to 0.6 $\mu$m, the improved method comprising:

(a) conducting blood in a forward direction into and through the fibers while maintaining a mean positive transmembrane pressure difference across the membranes from inlets to outlets of the hollow fibers;

(b) conducting blood in an external circuit from a region near the outlets of the fibers to a region near the inlets of the fibers or, alternatively, from a region near the inlets of the fibers to a region near the outlets of the fibers;

(c) collecting plasma-depleted blood from the outlets of the hollow fibers; and (d) collecting plasma which has passed through the pores of the membranes, the effective length of the hollow fibers being such that the L/D ratio is no greater than 16,400 cm$^{-1}$ D (L and D being in centimeters) and the velocity of the blood in step (a) being such that the shear rate is 200 to 2500 sec$^{-1}$, preferably 2400 to 2500 sec$^{-1}$.

The pulsed flow mode of the invention can be described as an improved method for plasmapheresis carried out in a system with a bundle consisting of a plurality of blood wettable porous membrane hollow fibers all of which are in parallel bundle alignment and have open inlet ends and open outlet ends, each fiber having a lumen diameter (D) of no greater than 0.050 cm, preferably 0.015 to 0.050 cm, the pore size of the porous membrane being within the range 0.1 to 1.0 μm (preferred membranes have pores which are of substantially uniform size within the range 0.4 to 0.6 μm), the improvement characterized in that the plasmapheresis can be carried out continuously, the improved method comprising:

(a) conducting blood in a forward direction into and through the fibers while maintaining a mean positive transmembrane pressure difference across the membranes from inlets to outlets of the hollow fibers;

(b) terminating the forward conducting of blood;

(c) conducting blood through the hollow fibers in the reverse direction;

(d) collecting plasma-depleted blood from the outlets of the hollow fibers;

(e) collecting plasma which has passed through the pores of the membranes; and (f) repeating in sequence steps (a), (b) and (c) to collect additional plasma-depleted blood and plasma, the effective length of the hollow fibers being such that the L/D ratio is no greater than 16,400 cm$^{-1}$ D (L and D being in centimeters) and the velocity of the blood in steps (a) and (c), except at the beginning and end of each step, being such that the shear rate is 200 to 2500 sec$^{-1}$, preferably 1000 to 1200 sec$^{-1}$.

In the pulsed flow method, the volume of blood conducted in either of step (a) or step (c) is at least 5% of the total volume of blood in the system. Further regarding this mode of the invention, it is to be understood that the transmembrane pressure difference across the membranes is negative for part of the distance that the blood is conducted across the membranes. In carrying out the pulsed flow mode, the arithmetic product of: (a) the time-average of the transmembrane pressure while it is positive in a portion of the fiber and (b) the time in that portion of the fiber is greater than such product when the transmembrane pressure is negative.

The following examples illustrate the process and module of the invention. The module used in each example, unless otherwise noted, comprised blood wettable polypropylene fibers (prepared by known procedures and commercially available) having a 330 μm lumen, a 610 μm outer diameter, pores which were 0.5 μm in diameter, and a porosity of 70% (that is, 70% open areas). The fibers were encased in a tube made of Lucite ® acrylic resin and potted with a polyurethane resin. The effective length of the fibers, that is, the usable length of the fibers, which is the portion outside the potted regions, is shown in each example.

Steady State Flow (Examples 1-4)

EXAMPLE 1

The module used in this example had 90 fibers, an effective length of 6.35 cm and an L/D of 192. Two units of anticoagulated whole blood were combined, adjusted to an hematocrit (hct.) of 38% with saline and conducted through the module by a peristaltic pump. Conditions and results are reported in Table 1 wherein $Q_{pc}$ is the rate of exit (plasma-depleted) blood and $Q_p$ is the rate of exit plasma, both in g/minute. After about 60 minutes the plasma-depleted blood outlet pressure suddenly dropped to zero. The cause was a block in the module inlet caused by an aggregation which is believed to have been the result of the incompatibility of the two units of blood. The results, however, are consistent with results of other experiments reported herein and, therefore, it is believed that the incompatibility did not materially detract from the value of the experiment as a demonstration of the invention.

TABLE 1

| Elapsed time (min) | $Q_{pc}$ (g/min) | $Q_p$ (g/min) | Pressure (mm Hg) Inlet | Pressure (mm Hg) Outlet | Plasma flux (mL/min/cm$^2$) | Outlet hct |
|---|---|---|---|---|---|---|
| 6 | 7.38 | 0.78 | 50 | 25 | 0.013 | 42 |
| 15 | 7.28 | 0.63 | 50 | 30 | 0.011 | 41 |
| 26 | 6.97 | 0.61 | 50 | 30 | 0.010 | 41 |
| 33 | 3.50 | 0.82 | 115 | 100 | 0.014 | 47 |
| 43 | 3.32 | 0.42 | 125 | 105 | 0.007 | 43 |
| 50 | 3.52 | 0.42 | 110 | 85 | 0.007 | 43 |
| 55 | 11.88 | 0.83 | 100 | 60 | 0.014 | 41 |

There was no visual evidence of hemolysis.

The rate of introduction of whole blood ($Q_{wb}$) may be obtained in this and in the other examples and in the experiment by combining $Q_{pc}$ and $Q_p$.

EXAMPLE 2

The module used in this example had 90 fibers, an effective length of 8.9 cm and an L/D of 270. Two units of anticoagulated whole blood were combined, adjusted to an hct of 37%, and conducted through the module by a peristaltic pump. Conditions and results are reported in Table 2.

TABLE 2

| Elapsed time (min) | $Q_{pc}$ (g/min) | $Q_p$ (g/min) | Pressure (mm Hg) Inlet | Pressure (mm Hg) Outlet | Plasma flux (mL/min/cm$^2$) | Outlet hct |
|---|---|---|---|---|---|---|
| 7 | 2.79 | 0.93 | 60 | 45 | 0.011 | 49 |
| 13 | 2.63 | 0.91 | 65 | 48 | 0.011 | 50 |
| 18 | 10.55 | 1.32 | 55 | 20 | 0.016 | 42 |
| 27 | 10.32 | 1.23 | 55 | 15 | 0.015 | 41 |
| 36 | 5.92 | 1.31 | 105 | 75 | 0.016 | 45 |
| 43 | 6.22 | 1.12 | 105 | 75 | 0.014 | 44 |
| 51 | 5.63 | 1.28 | 120 | 95 | 0.015 | 45 |
| 57 | 2.68 | 0.83 | 165 | 150 | 0.010 | 48 |
| 66 | 2.82 | 1.01 | 170 | 155 | 0.012 | 50 |
| 77 | 10.52 | 1.40 | 160 | 120 | 0.017 | 42 |
| 86 | 10.57 | 1.11 | 165 | 110 | 0.013 | 41 |

There was no visual evidence of hemolysis.

EXAMPLE 3

The module used in this example had 90 fibers, an effective length of 11.4 cm and an L/D of 346. Two units of anticoagulated whole blood were combined, adjusted to an hct. of 38%, and conducted through the module by a peristaltic pump. Conditions and results are reported in Table 3.

TABLE 3

| Elapsed time (min) | $Q_{pc}$ (g/min) | $Q_p$ (g/min) | Pressure (mm Hg) Inlet | Pressure (mm Hg) Outlet | Plasma flux (mL/min/cm$^2$) | Outlet hct (%) |
|---|---|---|---|---|---|---|
| 6 | 5.30 | 1.02 | 235 | 165 | 0.010 | 45 |
| 11 | 7.32 | 1.13 | 235 | 140 | 0.010 | 44 |
| 16 | 6.18 | 0.98 | 230 | 140 | 0.009 | 44 |
| 21 | 5.48 | 0.80 | 75 | 25 | 0.008 | 44 |
| 26 | 6.83 | 0.68 | 80 | 25 | 0.006 | 42 |
| 32 | 6.68 | 0.72 | 80 | 25 | 0.007 | 42 |
| 36 | 6.82 | 0.88 | 90 | 30 | 0.008 | 43 |
| 42 | 9.43 | 1.34 | 150 | 70 | 0.012 | 43 |
| 49 | 10.71 | 1.24 | 150 | 85 | 0.011 | 42 |
| 54 | 10.70 | 1.40 | 155 | 95 | 0.013 | 43 |
| 63 | 3.53 | 0.55 | 150 | 115 | 0.005 | 44 |
| 67 | 3.62 | 0.52 | 160 | 120 | 0.005 | 43 |

Hemolysis was visually observed in plasma collected while the inlet pressure was about 230 mm Hg. After the pressure was lowered, the plasma cleared and no further hemolysis was observed.

EXAMPLE 4

The module used in this example had 90 fibers, an effective length of 12.7 cm and an L/D of 385. One unit of anticoagulated whole blood, adjusted to an hct. of 38%, was conducted through the module by a peristaltic pump. Conditions and results are reported in Table 4.

pressure to which the blood was subjected. Scanning, by measuring light transmission using conventional procedures, at 650 to 500 nm indicated hemoglobin levels of 5.0 mg/dL in the sample taken at 54 min and 37.6 mg/dL in the sample taken at 58 min.

Reciprocatory Pulsatile Flow (Examples 5–9)

EXAMPLE 5

The module used in this example had 90 fibers, an effective length of 8.9 cm and an L/D of 270. Two units of anticoagulated whole blood were combined, adjusted to an hct. of 38%, and conducted through the module by a peristaltic pump. To minimize membrane fouling, the blood was conducted by reciprocatory pulsatile flow by means of a peristaltic pump on a line extending from the inlet to the outlet of the module, in accordance with the techniques disclosed in my earlier-filed applications. Conditions and results are reported in Table 5. The pulsed flow D. S. number (Duggins-Shaposka number) is defined as the ratio of the shear rate effects to the effects due to the rate at which whole blood is supplied to the unit.

$$\text{Pulsed Flow } D.S. \text{ Number} = \frac{Q_{wb} + Q_{pulse}}{Q_{wb}}$$

$Q_{wb}$ = the flow rate of whole blood
$Q_{pulse}$ = the flow rate of pulsed blood
At steady state conditions, that is, without pulsing, the D. S. number is 1.

TABLE 5

| Elapsed time (min) | $Q_{pc}$ (g/min) | $Q_p$ (g/min) | Pulse volume (mL) Forward | Pulse volume (mL) Reverse | Pulse frequency (oscillations) per min | D.S. # | Inlet Pressure (mm Hg) Max. | Inlet Pressure (mm Hg) Min. | Outlet Pressure (mm Hg) Max. | Outlet Pressure (mm Hg) Min. | Plasma flux (mL/min/cm$^2$) | Outlet hct (%) |
|---|---|---|---|---|---|---|---|---|---|---|---|---|
| 8 | 6.02 | 1.71 | 0.04 | 0.04 | 40 | 1.4 | 90 | 65 | 55 | 35 | 0.020 | 49 |
| 13 | 6.37 | 1.52 | 0.04 | 0.04 | 40 | 1.4 | 80 | 50 | 45 | 20 | 0.018 | 47 |
| 19 | 6.74 | 1.20 | 0.04 | 0.04 | 40 | 1.4 | 70 | 30 | 30 | 10 | 0.014 | 45 |
| 23 | 2.12 | 1.84 | 0.14 | 0.14 | 40 | 3.9 | 95 | −30 | 70 | −45 | 0.022 | 71 |
| 27 | 3.02 | 1.78 | 0.14 | 0.14 | 40 | 3.4 | 100 | −40 | 55 | −45 | 0.021 | 60 |
| 30 | 2.86 | 1.68 | 0.14 | 0.14 | 40 | 3.5 | 100 | −40 | 55 | −45 | 0.020 | 60 |
| 37 | 3.23 | 2.01 | 0.14 | 0.14 | 40 | 3.2 | 150 | 10 | 120 | −10 | 0.024 | 62 |
| 44 | 0.42 | 0.44 | 0.30 | 0.30 | 40 | 29.0 | 110 | <−50 | 25 | −50 | 0.005 | 78 |
| 50 | 0.78 | 0.68 | 0.30 | 0.30 | 40 | 17.5 | 105 | <−50 | 20 | −50 | 0.008 | 71 |
| 58 | 5.88 | 2.66 | 0.22 | 0.22 | 40 | 3.0 | 90 | <−50 | 5 | −25 | 0.032 | 55 |
| 63 | 5.62 | 2.32 | 0.22 | 0.22 | 40 | 3.2 | 120 | <−50 | 5 | −30 | 0.028 | 54 |
| 70 | 0.68 | 0.62 | 0.07 | 0.07 | 40 | 5.4 | 80 | −25 | 50 | −5 | 0.007 | 73 |
| 76 | 0.51 | 0.51 | 0.07 | 0.07 | 40 | 6.6 | 75 | −30 | 45 | −5 | 0.006 | 76 |
| 83 | 6.22 | 1.78 | 0.11 | 0.18 | 40 | 2.5 | 150 | 0 | 40 | −30 | 0.021 | 49 |
| 86 | 6.48 | 1.61 | 0.18 | 0.11 | 40 | 2.5 | 105 | −20 | 75 | −15 | 0.019 | 47 |
| 90 | 6.62 | 1.40 | 0.18 | 0.11 | 70 | 3.5 | 110 | −35 | 110 | −50 | 0.017 | 46 |

TABLE 4

| Elapsed time (min) | $Q_{pc}$ (g/min) | $Q_p$ (g/min) | Pressure (mm Hg) Inlet | Pressure (mm Hg) Outlet | Plasma flux (mL/min/cm$^2$) | Outlet hct (%) |
|---|---|---|---|---|---|---|
| 9 | 9.10 | 1.35 | 50 | −7 | 0.011 | 44 |
| 14 | 8.60 | 1.45 | 87 | 23 | 0.012 | 44 |
| 28 | 9.48 | 0.90 | 87 | 21 | 0.007 | 42 |
| 35 | 8.91 | 1.35 | 110 | 42 | 0.011 | 44 |
| 45 | 9.80 | 1.28 | 138 | 45 | 0.010 | 43 |
| 50 | 9.23 | 1.05 | 135 | 60 | 0.009 | 42 |
| 54 | 7.05 | 3.18 | 270 | 180 | 0.027 | 55 |
| 58 | 6.02 | 2.82 | 450 | 335 | 0.024 | 56 |

Hemolysis was visually observed in the last two plasma samples collected, thought to be due to the high There was no visual evidence of hemolysis. These results show that improved plasma flux and outlet hct. can be achieved by use of reciprocatory pulsatile flow.

EXAMPLE 6

The module used in this example had 30 fibers, an effective length of 6.4 cm and an L/D of 192. Whole blood, having an hct. of 41% adjusted to 38% with saline, was conducted through the module by means of a peristaltic pump. To minimize membrane fouling, the blood was conducted by reciprocatory pulsatile flow, with the inlet and outlet of the module being connected by a loop, in accordance with techniques disclosed in my earlier-filed applications. Conditions and results are reported in Table 6.

TABLE 6

| Elapsed time (min) | $Q_{pc}$ (g/min) | $Q_p$ (g/min) | Pulse volume (mL) Forward | Pulse volume (mL) Reverse | Pulse frequency (oscillations per min) | D.S. # | Inlet Pressure (mm Hg) Max. | Inlet Pressure (mm Hg) Min. | Outlet Pressure (mm Hg) Max. | Outlet Pressure (mm Hg) Min. | Plasma flux (mL/min/cm²) | Outlet hct (%) |
|---|---|---|---|---|---|---|---|---|---|---|---|---|
| 7 | 3.88 | 0.82 | 0.04 | 0.04 | 40 | 1.7 | 90 | 65 | 70 | 50 | 0.014 | 46 |
| 12 | 3.62 | 0.78 | 0.04 | 0.04 | 40 | 1.7 | 85 | 60 | 65 | 45 | 0.013 | 46 |
| 16 | 3.69 | 0.76 | 0.04 | 0.04 | 40 | 1.7 | 85 | 60 | 65 | 45 | 0.013 | 46 |
| 23 | 0.95 | 1.13 | 0.18 | 0.18 | 40 | 7.9 | 75 | −35 | 65 | −50 | 0.019 | 83 |
| 27 | 1.09 | 1.18 | 0.18 | 0.18 | 40 | 7.4 | 120 | −20 | 110 | −40 | 0.020 | 79 |
| 32 | 1.18 | 1.08 | 0.18 | 0.18 | 40 | 7.4 | 150 | 0 | 125 | −25 | 0.018 | 73 |
| 38 | 0.74 | 0.82 | 0.18 | 0.18 | 40 | 10.2 | 110 | −40 | 95 | <−50 | 0.014 | 80 |
| 43 | 0.68 | 0.62 | 0.18 | 0.18 | 40 | 12.1 | 105 | −45 | 90 | <−50 | 0.010 | 73 |
| 47 | 0.62 | 0.51 | 0.18 | 0.18 | 40 | 13.8 | 115 | −45 | 90 | <−50 | 0.008 | 69 |
| 55 | 7.13 | 1.32 | 0.11 | 0.11 | 40 | 2.0 | 75 | 5 | 30 | 0 | 0.022 | 45 |
| 60 | 6.64 | 1.45 | 0.11 | 0.11 | 40 | 2.0 | 70 | 10 | 40 | 5 | 0.024 | 46 |
| 65 | 6.79 | 1.51 | 0.11 | 0.11 | 40 | 2.0 | 75 | 10 | 40 | 5 | 0.025 | 46 |
| 73 | 3.16 | 1.93 | 0.26 | 0.26 | 40 | 5.1 | 90 | −50 | 60 | <−50 | 0.033 | 61 |
| 81 | 3.20 | 2.08 | 0.26 | 0.26 | 40 | 5.0 | 95 | −50 | 65 | <−50 | 0.035 | 63 |
| 85 | 2.82 | 1.93 | 0.26 | 0.26 | 40 | 5.4 | 90 | −50 | 65 | <−50 | 0.033 | 64 |

EXAMPLE 7

The module used in this example had 90 fibers, an effective length of 3.5 inches (8.9 cm), an active membrane surface area of 83 cm², and an L/D of 269. All tubing in the system was ⅛" (3.2 mm) I.D. and a micrometer valve was used in the blood outlet line to regulate pressure. One unit (net 524 g) of O positive whole blood having an hematocrit of 34% was used. Plasmapheresis was carried out for 71 minutes, at which time the blood supply was exhausted. During the first 17 minutes the module was operated in the steady state mode; the remainder of the run was carried out using the pulsed flow mode. The pulsed flow data are shown in Table 7.

TABLE 7

| Elapsed time (min) | $Q_{pc}$ (g/min) | $Q_p$ (g/min) | Pulse volume (mL) Forward | Pulse volume (mL) Reverse | Pulse frequency (oscillations per min) | Inlet Pressure (mm Hg) Max. | Inlet Pressure (mm Hg) Min. | Outlet Pressure (mm Hg) Max. | Outlet Pressure (mm Hg) Min. | Plasma flux (mL/min/cm²) | Outlet hct (%) |
|---|---|---|---|---|---|---|---|---|---|---|---|
| 21 | 3.71 | 1.00 | 0.3 | 0.3 | 10 | 125 | 100 | 110 | 75 | 0.012 | 43 |
| 24 | 3.85 | 1.10 | 0.3 | 0.3 | 10 | 150 | 60 | 125 | 75 | 0.013 | 44 |
| 28 | 3.68 | 1.33 | 0.3 | 0.3 | 20 | 150 | 50 | 125 | 60 | 0.016 | 46 |
| 32 | 3.62 | 1.30 | 0.3 | 0.3 | 20 | 150 | 60 | 135 | 75 | 0.016 | 46 |
| 36 | 4.10 | 1.24 | 0.3 | 0.3 | 30 | 150 | 50 | 120 | 40 | 0.015 | 44 |
| 40 | 4.42 | 1.00 | 0.3 | 0.3 | 30 | 115 | 20 | 80 | 15 | 0.012 | 42 |
| 45 | 3.22 | 2.29 | 0.62 | 0.62 | 30 | 135 | −15 | 105 | −45 | 0.028 | 58 |
| 48 | 3.86 | 1.98 | 0.62 | 0.62 | 30 | 125 | −25 | 95 | −50 | 0.024 | 51 |
| 53 | 3.08 | 1.49 | 0.62 | 0.62 | 40 | 105 | −100 | 60 | −80 | 0.018 | 50 |
| 60 | 2.89 | 1.75 | 0.46 | 0.46 | 40 | 80 | −65 | 50 | −65 | 0.021 | 55 |
| 64 | 2.90 | 1.71 | 0.46 | 0.46 | 40 | 100 | −70 | 45 | −65 | 0.021 | 54 |
| 69 | 3.57 | 1.74 | 0.3 | 0.3 | 40 | 90 | −25 | 75 | −50 | 0.021 | 51 |

EXAMPLE 8

The module used in this example had 708 fibers, an effective length of 5.625 inches (14.3 cm), an active membrane surface area of 1,050 cm², and an L/D of 433. The whole blood inlet and plasma outlet lines were ⅛ inch (3.2 mm) I.D. and the plasma-depleted blood and pulser loop lines were 3/16 inch (4.8 mm) I.D. The pressure was adjusted on the blood outlet line with a hose clamp. Two units (net 537 g and 566 g) of O positive whole blood having a hematocrit of 39.5%, diluted to 38.5% with sterile saline, were used. Plasmapheresis was carried out rapidly for 46 minutes at about a 40 ml/min whole blood throughput rate. The supply of blood was depleted in about 15 minutes, after which the plasma-depleted and plasma fractions were combined and rerun through the module. Recombination of fractions was effected twice during the run. The pulse frequency was 40 cycles/min. The data for this run are shown in Table 8; data were collected at 8 intervals (1 min each) uniformly spaced throughout the 46 minute run.

TABLE 8

| $Q_{pc}$ (g/min) | $Q_p$ (g/min) | Pulse volume (mL) Forward | Pulse volume (mL) Reverse | Plasma flux (mL/min/cm²) | Outlet hct (%) |
|---|---|---|---|---|---|
| 23.77 | 14.61 | 1.37 | 1.27 | 0.014 | 62 |
| 25.35 | 11.91 | 1.37 | 1.63 | 0.011 | 57 |
| 25.80 | 12.03 | 1.37 | 1.63 | 0.011 | 55 |
| 21.75 | 15.99 | 1.37 | 1.27 | 0.015 | 67 |
| 27.83 | 16.43 | 1.37 | 1.31 | 0.016 | 61 |
| 27.22 | 14.91 | 1.37 | 1.31 | 0.013 | 60 |
| 23.41 | 14.64 | 1.37 | 1.31 | 0.014 | 63 |
| 26.48 | 11.65 | 1.31 | 1.27 | 0.011 | 55 |

EXAMPLE 9

The module used in this example was similar to that used in Example 8, except that the plasma-depleted blood outlet and the plasma outlet were connected back to the whole blood supply so that the system could be run continuously for almost 4 hours. Two units (net 540.6 g each) of O positive whole blood having an hematocrit of 40.5% were used and the module and tubing were filled with sterile saline. Plasmapheresis was carried out for 30 minutes to effect dilution of the whole blood and the saline to an hematocrit of 36%. The pulse frequency was 40 cycles/min. as in Example 8. Data were collected every 30 minutes during the run and are shown in Table 9.

When the pressure was lowered, plasmapheresis continued satisfactorily.

TABLE 11

| Elapsed time (min) | $Q_{pc}$ (g/min) | $Q_p$ (g/min) | Recycle flow rate (mL/min) | Pressure (mm Hg) Inlet | Pressure (mm Hg) Outlet | Plasma flux (mL/min/cm$^2$) | Outlet hct (%) | D.S. # |
|---|---|---|---|---|---|---|---|---|
| 5 | 2.89 | 1.75 | 26 | 295 | −20 | 0.012 | 61 | 6.6 |
| 11 | 3.35 | 1.29 | 26 | 260 | −20 | 0.009 | 53 | 6.6 |
| 16 | 3.71 | 0.94 | 26 (RF) | −35 | 100 | 0.007 | 48 | 6.6 |
| 29 | 4.41 | 0.46 | 4 | 80 | 65 | 0.003 | 42 | 1.8 |
| 42 | 0.00 | 0.96 | 19.5 | >350 | −20 | 0.007 | — | 21.3 |
| 52 | 7.69 | 0.98 | 12 | 85 | −20 | 0.007 | 43 | 2.4 |
| 57 | 7.49 | 1.02 | 12 | 80 | −20 | 0.007 | 43 | 2.4 |
| 62 | 7.69 | 0.53 | 12 (RF) | 70 | 100 | 0.004 | 41 | 2.5 |

TABLE 9

| $Q_{pc}$ (g/min) | $Q_p$ (g/min) | Pulse volume (mL) Forward | Pulse volume (mL) Reverse | Plasma flux (mL/min/cm$^2$) | Outlet hct (%) |
|---|---|---|---|---|---|
| 19.87 | 17.30 | 1.37 | 1.27 | 0.016 | 67 |
| 21.35 | 15.93 | 1.37 | 1.27 | 0.015 | 65 |
| 20.58 | 17.06 | 1.37 | 1.27 | 0.016 | 66 |
| 20.79 | 16.71 | 1.37 | 1.27 | 0.016 | 65 |
| 20.15 | 17.20 | 1.37 | 1.27 | 0.016 | 67 |
| 21.36 | 16.04 | 1.37 | 1.27 | 0.015 | 63 |
| 20.88 | 16.97 | 1.37 | 1.27 | 0.016 | 65 |

During the entire run of 230 min, 3850.2 mL of plasma was produced at a rate of 16.7 mL/min.

Recycle Flow (Examples 10 and 11)

EXAMPLE 10

This example was carried out to demonstrate the recycle flow mode of the invention. The module had 90 fibers, an effective length of 3.5 inches (8.9 cm) and an L/D of 269. The whole blood used had an hematocrit of 38%. Conditions and results are reported in Table 10. In the table, RF indicates that the recycle flow was reversed. Although such reversal thus is outside the embodiment of FIG. 2, the results achieved prior and subsequent to the reversal were not adversely affected and, moreover, the results achieved during the reversal were comparable to those achieved with the embodiment of FIG. 2. Therefore, it has been concluded that the liquid in the recycle loop can flow in either direction in this mode of the invention.

TABLE 10

| Elapsed time (min) | $Q_{pc}$ (g/min) | $Q_p$ (g/min) | Recycle flow rate (mL/min) | Pressure (mm Hg) Inlet | Pressure (mm Hg) Outlet | Plasma flux (mL/min/cm$^2$) | Outlet hct (%) | D.S. # |
|---|---|---|---|---|---|---|---|---|
| 3 | 7.01 | 1.16 | 22.5 | 100 | −15 | 0.014 | 44 | 3.8 |
| 17 | 6.68 | 1.27 | 22.5 (RF) | 50 | 100 | 0.015 | 45 | 3.8 |
| 23 | 7.57 | 0.74 | 0 | 70 | 30 | 0.009 | 42 | 1.0 |
| 28 | 0 | 0 | 29.5 | 150 | −10 | — | — | — |
| 48 | 1.00 | 0.20 | 29.5 (RF) | −30 | 75 | 0.0024 | 46 | 30.7 |
| 68 | 0.74 | 0.35 | 7.5 | 80 | 10 | 0.004 | 56 | 7.9 |
| 78 | 0.72 | 0.38 | 7.5 (RF) | 40 | 80 | 0.0045 | 58 | 7.8 |
| 86 | 4.09 | 0.60 | 15 | 75 | −15 | 0.007 | 44 | 4.2 |
| 93 | 3.96 | 0.70 | 15 (RF) | 50 | 75 | 0.008 | 45 | 4.2 |
| 100 | 3.91 | 0.62 | 15 | 85 | 0 | 0.007 | 44 | 4.3 |

EXAMPLE 11

Example 10 was repeated except that the fiber effective length was 6 inches (15.2 cm) and the L/D was 462. Conditions and results are reported in Table 11. After 42 minutes the inlet pressure exceeded 350 mm Hg, resulting in severe hemolysis and the $Q_{pc}$ dropped to 0.

Steady State Flow Experiment (A Comparative Example)

The module used in this experiment is presently commercially available. It had 2520 fibers of the same kind used in Examples 1 to 11, an effective length of 24 cm and an L/D of 728. Two units of anticoagulated whole blood were combined, adjusted to an hct. of 37%, and conducted through the module by a peristaltic pump. Exit (plasma-depleted) blood and plasma which were collected during the procedure were admixed and returned through the module four times so that the length of the experiment could be extended to ensure steady state conditions. Because the results throughout the run were consistent, it was concluded, as in Examples 8 and 9, that the use of recombined blood did not materially affect the results of this experiment. Conditions and results are reported in Table 12.

TABLE 12

| Elapsed time (min) | $Q_{pc}$ (g/min) | $Q_p$ (g/min) | Pressure (mm Hg) Inlet | Pressure (mm Hg) Outlet | Plasma flux (mL/min/cm$^2$) | Outlet hct (%) |
|---|---|---|---|---|---|---|
| 3 | 72.7 | 28.10 | 135 | 120 | 0.006 | 51 |
| 6 | 80.5 | 28.90 | 125 | 110 | 0.006 | 50 |
| 9 | 84.2 | 28.90 | 135 | 120 | 0.006 | 50 |
| 12 | 84.7 | 27.90 | 150 | 130 | 0.006 | 49 |
| 14 | 79.0 | 32.60 | 130 | 110 | 0.007 | 52 |
| 17 | 84.7 | 26.60 | 170 | 140 | 0.005 | 49 |
| 19 | 78.3 | 28.40 | 145 | 115 | 0.006 | 50 |
| 22 | 80.8 | 27.40 | 155 | 125 | 0.006 | 49 |
| 24 | 60.2 | 22.10 | 175 | 160 | 0.004 | 50 |
| 29 | 59.2 | 21.30 | 175 | 160 | 0.004 | 50 |

There was no visual evidence of hemolysis. Comparison of these results with the results of Examples 1, 2 and 3 reveals that improved plasma flux with substantially equivalent outlet hct were achieved using the modules of the invention, which modules had approximately one-fourth to one-half of the volume of the module used in this experiment for comparison. In order to better compare these results with results attained using the modules of the invention, the results of Examples 1, 2 and 3 were normalized to the conditions of this experiment by use of a regression equation derived from the above test data. These calculated results are tabulated in Table 13 to show the predicted outlet hct and plasma flux using the modules of the invention at the conditions existing at the time intervals reported in this experiment. Data from Table 12 are repeated to show the actual (measured) results from the experiment.

100 to about 350, in accordance with the aforesaid formula for L/D.

Using regression analysis to evaluate other plasmapheresis data obtained by means of the instant invention (not included in this specification), Table 14 was assembled to show the expected performance of the hollow fiber module of the invention under steady flow conditions (D.S. number of 1) and under conditions of reciprocatory pulsatile flow (D.S. numbers of 3 to 9). Pulsed flow D.S. number (Duggins-Shaposka number) has been defined in Example 5. Table 14 thus shows the predicted outlet hct and plasma flux at various length to

TABLE 13

Outlet Hct (%) and Plasma Flux (mL/min/cm$^2$): Predicted for Module Lengths of Examples 1, 2 and 3 and Actual for Module of the Experiment

| Elapsed time (min) | Predicted Ex. 1 (L/D = 192) | Ex. 2 (L/D = 270) | Ex. 3 (L/D = 346) | Measured Exp. (L/D = 728) | Predicted Exp. |
|---|---|---|---|---|---|
| 3 | 45 | 47 | 49 | 51 | 52 |
|   | 0.010 | 0.008 | 0.007 | 0.005 | 0.005 |
| 6 | 45 | 47 | 48 | 50 | 52 |
|   | 0.010 | 0.009 | 0.008 | 0.005 | 0.005 |
| 9 | 45 | 46 | 48 | 50 | 51 |
|   | 0.010 | 0.009 | 0.008 | 0.005 | 0.005 |
| 12 | 44 | 46 | 48 | 49 | 51 |
|   | 0.010 | 0.009 | 0.008 | 0.005 | 0.005 |
| 14 | 45 | 47 | 48 | 52 | 51 |
|   | 0.010 | 0.009 | 0.008 | 0.006 | 0.005 |
| 17 | 44 | 46 | 47 | 49 | 50 |
|   | 0.010 | 0.008 | 0.007 | 0.005 | 0.005 |
| 19 | 45 | 47 | 48 | 50 | 51 |
|   | 0.010 | 0.008 | 0.007 | 0.005 | 0.005 |
| 22 | 44 | 46 | 48 | 50 | 51 |
|   | 0.010 | 0.008 | 0.007 | 0.005 | 0.005 |
| 24 | 45 | 47 | 49 | 51 | 52 |
|   | 0.008 | 0.007 | 0.006 | 0.004 | 0.004 |
| 29 | 45 | 47 | 49 | 50 | 52 |
|   | 0.008 | 0.007 | 0.006 | 0.004 | 0.004 |
| Avg. | 45 | 47 | 48 | 50 | 51 |
|   | 0.010 | 0.008 | 0.007 | 0.005 | 0.005 |
| Std. Dev'n. | 0.48 | 0.52 | 0.63 | 0.92 | 0.67 |
|   | 0.0008 | 0.0008 | 0.0002 | 0.0006 | 0.0004 |

It is to be understood that although the regression equation was calculated based on the actual results of Examples 1, 2 and 3, there may be some error in the predicted results. It is believed, however, that any error is small (see standard deviation). Using the results of Examples 1 to 4 and other experiments not reported herein in regression equations, it has been predicted that hollow fiber modules having fibers with lumen diameters smaller or larger than 330 μm are useful and are within the invention provided the equivalent L/D at 330 μm is less than about 530, preferably being about diameter (L/D) ratios at various effective fiber lengths at various D.S. numbers. All units from which the data were collected were comprised of blood wettable polypropylene fibers of 330 μm lumen diameter, 610 μm outer diameter and pores of 0.5 μm diameter. The through-put was 0.036 mL/minute/fiber at an inlet pressure of 75 mm of Hg. The inlet hct of the blood was 38%. It may be seen from Table 14 that when the L/D ratio exceeded about 540, the outlet hematocrit and plasma flux values decreased to less acceptable levels.

TABLE 14

Outlet Hct (%) and Plasma Flux (mL/min/cm$^2$)

| L/D | Length in Inches (cm) | D.S. Numbers 1 | 3 | 4 | 5 | 6 | 7 | 8 | 9 |
|---|---|---|---|---|---|---|---|---|---|
| 192 | 2.5 | 46.04 | 57.85 | 62.74 | 66.11 | 67.95 | 68.27 | 67.07 | 64.33 |
|  | (6.4) | 0.010 | 0.019 | 0.022 | 0.023 | 0.024 | 0.024 | 0.024 | 0.022 |
| 231 | 3.0 | 47.22 | 60.44 | 65.00 | 68.03 | 69.54 | 69.53 | 67.99 | 64.93 |
|  | (7.6) | 0.009 | 0.017 | 0.019 | 0.020 | 0.021 | 0.021 | 0.020 | 0.019 |
| 269 | 3.5 | 48.30 | 62.54 | 66.77 | 69.48 | 70.66 | 70.31 | 68.44 | 65.04 |
|  | (8.9) | 0.008 | 0.015 | 0.017 | 0.018 | 0.018 | 0.018 | 0.017 | 0.016 |
| 308 | 4.0 | 49.30 | 64.17 | 68.07 | 70.44 | 71.29 | 70.61 | 68.40 | 64.68 |
|  | (10.2) | 0.008 | 0.014 | 0.015 | 0.016 | 0.016 | 0.016 | 0.015 | 0.014 |
| 346 | 4.5 | 50.22 | 65.32 | 68.89 | 70.93 | 71.44 | 70.43 | 67.89 | 63.83 |
|  | (11.4) | 0.007 | 0.013 | 0.014 | 0.014 | 0.014 | 0.014 | 0.013 | 0.012 |
| 385 | 5.0 | 51.05 | 65.99 | 69.22 | 70.93 | 71.11 | 69.77 | 66.90 | 62.51 |
|  | (12.7) | 0.007 | 0.012 | 0.012 | 0.013 | 0.013 | 0.012 | 0.012 | 0.011 |
| 423 | 5.5 | 51.79 | 66.18 | 69.08 | 70.46 | 70.31 | 68.63 | 65.43 | 60.71 |

TABLE 14-continued

| | | Outlet Hct (%) and Plasma Flux (mL/min/cm$^2$) | | | | | | | |
|---|---|---|---|---|---|---|---|---|---|
| | Length in | D.S. Numbers | | | | | | | |
| L/D | Inches (cm) | 1 | 3 | 4 | 5 | 6 | 7 | 8 | 9 |
| | (14.0) | 0.007 | 0.011 | 0.011 | 0.011 | 0.011 | 0.011 | 0.010 | 0.009 |
| 462 | 6.0 | 52.44 | 65.90 | 68.46 | 69.51 | 69.02 | 67.02 | 63.48 | 58.43 |
| | (15.2) | 0.006 | 0.010 | 0.010 | 0.010 | 0.010 | 0.010 | 0.009 | 0.008 |
| 500 | 6.5 | 53.01 | 65.13 | 67.37 | 68.08 | 67.26 | 64.92 | 61.06 | 55.67 |
| | (16.5) | 0.006 | 0.009 | 0.009 | 0.009 | 0.009 | 0.009 | 0.008 | 0.007 |
| 539 | 7.0 | 53.50 | 63.88 | 65.79 | 66.17 | 65.02 | 62.35 | 58.15 | 52.43 |
| | (17.8) | 0.006 | 0.008 | 0.008 | 0.008 | 0.008 | 0.008 | 0.007 | 0.005 |
| 577 | 7.5 | 53.89 | 62.16 | 63.73 | 63.78 | 62.30 | 59.29 | 54.76 | 48.71 |
| | (19.1) | 0.005 | 0.007 | 0.007 | 0.007 | 0.007 | 0.007 | 0.006 | 0.004 |
| 615 | 8.0 | 54.20 | 59.96 | 61.20 | 60.91 | 59.10 | 55.76 | 50.90 | 44.51 |
| | (20.3) | 0.005 | 0.006 | 0.006 | 0.006 | 0.006 | 0.005 | 0.004 | 0.002 |

It may be seen from the data in Table 14 that, at a given L/D ratio, there is an optimum degree of pulsatility (D.S. number) for achieving a maximum in hematocrit and/or a maximum in flux. One skilled in the art will understand that, in carrying out the plasmapheresis process of this invention, the operator usually selects a compromise between the highest attainable hematocrit and the highest attainable flux. For example, although the process of the invention can be carried out in such a way that a 90% hematocrit can be obtained in the plasma-depleted blood, the goal hematocrit usually is no greater than 70%; preferably, it is about 65%. As the goal hematocrit is lowered, the achievable flux is increased. Thus, although higher fluxes are achievable by means of the process of this invention, a flux of about 0.04 mL/minute/cm$^2$ represents a desirable compromise since, at this value an hematocrit of 65% is readily achievable. Such an achievable combination of flux and hematocrit represents a marked advance over art plasmapheresis processes and apparatus, particularly continuous plamapheresis and apparatus.

In addition to the aforesaid correlation between pulsatility, L/D ratio, hematocrit and flux, one skilled in the art will also recognize that these parameters are dependent on the flow rate of the whole blood flowing through the system. Finally, it is to be understood that all of the examples and the single experiment described herein, except for Examples 7 to 9, were carried out with whole blood adjusted to an hct of 37-38%, and that different results (hct and flux) would be obtained at different hematocrit starting levels. In general, when a plasmapheresis is carried out in the art, male blood which has a normal hematocrit of about 44-45% is diluted with anticoagulant to an hematocrit of about 38%; female blood which has a normal hematocrit of about 38% is diluted with anticoagulant to about 30%.

The following discussion is intended to supplement the aforesaid disclosure in that it outlines steps which one skilled in the art may follow in carrying out a plasmapheresis by means of the invention. In addition to definitions already provided, the following may be useful:

$$\text{Recycle D.S. number} = \frac{Q_{wb} + Q_{recycle}}{Q_{wb}} \quad (1)$$

$Q_{wb}$ = the flow rate of whole blood
$Q_{recycle}$ = the flow rate of recycle
$N$ = the number of fibers in the module (2)
The active surface area of the fibers $(A)$ = (3)
$\pi DNL$ wherein $D$ and $L$ are in cm $$\text{Shear rate (sec}^{-1}) = \frac{4(\text{flow velocity in cm/sec})}{\text{lumen radius in cm}} \quad (4)$$

Steady State Flow

1. Select a whole blood inlet feed rate $Q_{wb}$ based on treatment needs.
2. Select the whole blood inlet hematocrit based on availability.
3. Select the hematocrit for the outlet cellular-enriched fraction (maximum of 60% without hemolysis).
4. Calculate the outlet plasma flow $Q_p$ from steps 1-3.
5. Select diameter initially at 0.033 cm.
6. From the data given in Tables 14 and 15, select the desired plasma flux and outlet hematocrit. Note length in table and calculate whole blood flow/fiber from data in table, that is, 70 mL/min feed and 2,000 cm$^2$ surface area.
7. Calculate the whole blood shear rate to compare with data of Table 16.
8. Calculate the number of fibers needed from steps 1 and 6.
9. Calculate the membrame surface area.
10. If desired, select a different lumen diameter.
11. Calculate a new rate of whole blood flow per fiber to get the desired shear rate.
12. Calculate the number of fibers needed.
13. Calculate the fiber length needed to give the same area as before.
14. Calculate L/D to compare with data from above and in Table 16.

Recycle Steady State Flow

1. Follow the steps outlined above for steady state flow. Maximum hematocrit is 57-61 without hemolysis in accordance with Table 15 and the examples.
2. Select a cellular-enriched blood recycle rate that gives the selected peak shear rate (see Table 16).
3. Select lumen diameter initially at 0.033 cm.
4. Determine plasma flux and fiber length from Table 15, or alternatively from Tables 10 or 11.
5. Calculate number of fibers and surface area.
6. Use same procedure design for other diameters, keeping shear rate and area the same as before.

Reciprocatory Pulsatile Flow

1. Select a whole blood inlet feed rate $Q_{wb}$ based on treatment needs.
2. Select the outlet plasma flow $Q_p$.

3. Select the whole blood inlet hematocrit based on availability.

4. Select the hematocrit for the outlet cellular-enriched fraction based on treatment needs and goals.

5. Use an arbitrarily low L/D initially, for example, 100-200.

6. Assume a lumen diameter of 0.033 cm initially.

7. From the data given in Table 17 select the highest whole blood flow per fiber to give the desired hematocrit for the outlet cellular-enriched fraction at selected L/D.

8. Calculate the whole blood shear rate and adjust the whole blood flow per fiber $Q_{wb}$ to give the desired shear rate.

9. Calculate the number of fibers needed from $Q_{wb}$ and treatment requirements.

10. Calculate fiber length from $L = L/D \times D$.

11. Calculate the membrane surface area from number, diameter and length of fibers.

12. If desired, select a different lumen diameter.

13. Calculate a new rate of whole blood flow per fiber to get the selected shear rate.

14. Calculate as before the number of fibers needed.

15. Calculate the fiber length needed to give the same area.

16. Calculate L/D and compare with the data from Table 16.

17. Select the pulse frequency.

18. Calculate the required pulsed blood flow rate and select the pulsed blood volume and time during a ½ pulse.

19. Calculate the total blood flow rate per pulse for the desired peak shear rate and resulting D.S. number.

As suggested above, Table 16 includes data which may be used in connection with the aforesaid outlined steps for carrying out the three modes of operation of the invention.

TABLE 15

Comparison of the Expected Performance of Hollow Fibers with Constant Surface Area of 2000 cm² When Operated in Steady Flow (D.S. Number = 1) and Recycle Flow (D.S. Number >1) Modes, All Units Operating at a Thru-Put of 70 mL/min (Total) and an Inlet Pressure of 70 mm of Hg

| Length Inches (cm) | Steady | DS = 2 Re-cycle | DS = 4 Re-cycle | DS = 6 Re-cycle | DS = 8 Re-cycle | L/D |
|---|---|---|---|---|---|---|
| 2.5 H = (6.4) F = | 47.5 0.007 | — — | 47.7 0.007 | 49.1 0.007 | 50.9 0.008 | 192 |
| 3.0 H = (7.6) F = | 48.2 0.007 | — — | 47.4 0.006 | 49.4 0.008 | 51.9 0.009 | 231 |
| 3.5 H = (8.9) F = N = | 48.8 0.008 2170 | — — | 47.1 0.006 | 49.9 0.008 | 53.3 0.01 | 269 |
| 4.0 H = (10.2) F = | 49.2 0.008 | — — | 47 0.006 | 50.5 0.008 | 55 0.01 | 308 |
| 4.5 H = (11.4) F = | 49.5 0.008 | — — | 46.9 0.006 | 51.4 0.009 | 57 0.011 | 346 |
| 5.0 H = (12.7) F = N = | 49.6 0.008 1519 | 43 0.004 | 47 0.006 | 52.4 0.009 | — — | 385 |
| 5.5 H = (14.0) F = | 49.6 0.008 | 42.3 0.003 | 47.1 0.006 | 53.7 0.01 | — — | 432 |
| 6.0 H = (15.2) F = | 49.4 0.008 | 41.6 0.003 | 47.3 0.006 | 55.1 0.01 | — — | 462 |
| 6.5 H = (16.5) F = | 49.1 0.008 | — — | — — | — — | — — | 500 |
| 7.0 H = (17.8) F = | 48.7 0.008 | — — | — — | — — | — — | 539 |
| 7.5 H = (19.1) F = | 53.9 0.006 | — — | — — | — — | — — | — |
| 8.0 H = | 54.2 | — | — | — | — | — |

TABLE 15-continued

Comparison of the Expected Performance of Hollow Fibers with Constant Surface Area of 2000 cm² When Operated in Steady Flow (D.S. Number = 1) and Recycle Flow (D.S. Number >1) Modes, All Units Operating at a Thru-Put of 70 mL/min (Total) and an Inlet Pressure of 70 mm of Hg

| Length Inches (cm) | Steady | DS = 2 Re-cycle | DS = 4 Re-cycle | DS = 6 Re-cycle | DS = 8 Re-cycle | L/D |
|---|---|---|---|---|---|---|
| (20.3) F = | 0.006 | — | — | — | — | — |

TABLE 16

| Pulsed Flow | Minimum | Best Mode | Maximum |
|---|---|---|---|
| Hct in (%) | >0 | 38 | 90 |
| Hct out (%) | >0 | 65 | 90 |
| Lumen diameter D (cm) | 0.015 | 0.033 | 0.050 |
| Inlet feed pressure (mm Hg) at 0.5 μm pore diameter | 10 | 75-130 | 250 |
| Plasma flux (mL/min/cm²) | >0 | 0.042 | — |
| Whole blood shear rate (sec⁻¹) | 100 | 198 | 1200 |
| Pulsed blood peak shear rate (sec⁻¹) | 100 | 948 | 2500 |
| Peak shear rate (sec⁻¹) | 200 | 1146 | 2500 |
| Pulse frequency (cycles/min) | 20 | 40 | 80 |
| Pulse volume/½ pulse cycle (mL) | — | 1.2-1.4 | — |
| Duration of pulse/½ pulse cycle (sec) at 40 cycles/min | — | 0.75 | — |
| Pulse pressure (mm Hg) | — | −20 | — |
| Length of fibers (cm) at 0.5 μm pore diameter | >0 | 6.6 | 11.4 |
| L/D at D = 0.033 cm | — | 200 | 540 |
| Membrane surface area (cm²) | — | 1174 | — |
| Inlet flow rate $Q_{wb}$ (mL/min) | 10 | 72 | 400 |
| Whole blood flow rate/fiber (mL/min) | — | 0.042 | — |
| Peak flow rate/fiber (mL/min) | — | 0.244 | — |
| No. of fibers | — | 1713 | — |
| Plasma flow rate $Q_p$ (mL/min) | — | 30 | — |
| Blood outlet pressure (mm Hg) | — | −20 | — |
| Steady State Flow | | | |
| Hct in (%) | >0 | 38 | — |
| Hct out (%) | >0 | 49 | 60 |
| Lumen diameter D (cm) | 0.015 | 0.033 | 0.050 |
| Whole blood shear rate (sec⁻¹) | — | 94 | 2500 |
| Length of fibers (cm) | — | 6.3 | 8.9 |
| Inlet feed pressure (mm Hg) at 0.5 μm pore diameter | — | 75 | 250 |
| L/D at D = 0.033 cm | — | 192 | 300 |
| No. of fibers | — | 3469 | — |
| Membrane surface area (cm²) | — | 2285 | — |
| Inlet blood flow rate $Q_{wb}$ (mL/min) | — | 72 | — |
| Flow rate/fiber (mL/min) | — | 0.021 | — |
| Plasma flow rate $Q_p$ (mL/min) | — | 16 | — |
| Plasma flux (mL/min/cm²) | — | 0.007 | — |
| Minimum blood outlet pressure (mm Hg) at 0.5 μm pore diameter | — | 50 | <250 |
| Recycle Steady State Flow | | | |
| Hct in (%) | — | 38 | — |
| Hct out (%) | — | 55 | 57-61 |
| Lumen diameter D (cm) | 0.015 | 0.033 | 0.050 |
| Inlet feed pressure (mm Hg) | — | 70 | 250 |

TABLE 16-continued

| Pulsed Flow | Minimum | Best Mode | Maximum |
|---|---|---|---|
| Total blood flow shear rate (sec$^{-1}$) | — | 2450 | 2500 |
| Inlet blood flow rate $Q_{wb}$ (mL/min) | — | 65 | — |
| Recycle blood flow rate (mL/min) | — | 388 | — |
| Plasma flow rate $Q_p$ (mL/min) | — | 20 | — |
| No. of fibers | — | 1688 | — |
| Plasma flux (mL/min/cm$^2$) | — | 0.01 | — |
| Membrane surface area (cm$^2$) | — | 2000 | — |
| Length of fibers (cm) | — | 11.4 | — |
| L/D at D = 0.033 cm | — | 345 | 460 |
| Flow rate/fiber minimum | — | 0.268 | — |

TABLE 17

Pulsed Flow
Hematocrit vs L/D vs Flow/Fiber

| Flow Per Fib (mL/min) | L/D Ratio | | | | | | | | | | | |
|---|---|---|---|---|---|---|---|---|---|---|---|---|
| | 150 | 200 | 250 | 300 | 350 | 400 | 450 | 500 | 550 | 600 | 650 | 700 |
| 0.010 | 81.1 | 83.1 | 84.2 | 84.6 | 84.3 | 83.3 | 81.6 | 79.2 | 76.1 | 72.4 | 67.9 | 62.8 |
| 0.012 | 80.1 | 81.9 | 83.0 | 83.4 | 83.2 | 82.2 | 80.5 | 78.2 | 75.2 | 71.4 | 67.0 | 62.0 |
| 0.014 | 78.8 | 80.7 | 81.8 | 82.3 | 82.0 | 81.1 | 79.5 | 77.2 | 74.2 | 70.5 | 66.2 | 61.1 |
| 0.016 | 77.6 | 79.4 | 80.6 | 81.1 | 80.9 | 80.1 | 78.5 | 76.2 | 73.3 | 69.7 | 65.4 | 60.4 |
| 0.018 | 76.3 | 78.2 | 79.5 | 80.0 | 79.9 | 79.0 | 77.5 | 75.3 | 72.4 | 68.8 | 64.5 | 59.6 |
| 0.020 | 75.1 | 77.1 | 78.3 | 78.9 | 78.8 | 78.0 | 76.5 | 74.4 | 71.5 | 68.0 | 63.8 | 58.9 |
| 0.022 | 73.9 | 75.9 | 77.2 | 77.9 | 77.8 | 77.1 | 75.6 | 73.5 | 70.7 | 67.2 | 63.0 | 58.1 |
| 0.024 | 72.8 | 74.8 | 76.2 | 76.8 | 76.8 | 76.1 | 74.7 | 72.6 | 69.9 | 66.4 | 62.3 | 57.5 |
| 0.026 | 71.6 | 73.7 | 75.1 | 75.8 | 75.9 | 75.2 | 73.8 | 71.8 | 69.1 | 65.7 | 61.6 | 56.8 |
| 0.028 | 70.5 | 72.6 | 74.1 | 74.8 | 74.9 | 74.3 | 73.0 | 71.0 | 68.3 | 65.0 | 60.9 | 56.2 |
| 0.030 | 69.4 | 71.6 | 73.1 | 73.9 | 74.0 | 73.4 | 72.2 | 70.2 | 67.6 | 64.3 | 60.3 | 55.6 |
| 0.032 | 68.4 | 70.6 | 72.1 | 73.0 | 73.1 | 72.6 | 71.4 | 69.5 | 66.9 | 63.6 | 59.7 | 55.0 |
| 0.034 | 67.3 | 69.6 | 71.2 | 72.1 | 72.3 | 71.8 | 70.6 | 68.8 | 66.2 | 63.0 | 59.1 | 54.5 |
| 0.036 | 66.3 | 68.6 | 70.3 | 71.2 | 71.5 | 71.0 | 69.9 | 68.1 | 65.6 | 62.4 | 58.5 | 54.0 |
| 0.038 | 65.4 | 67.7 | 69.4 | 70.4 | 70.7 | 70.3 | 69.2 | 67.4 | 65.0 | 61.8 | 58.0 | 53.5 |
| 0.040 | 64.4 | 66.8 | 68.5 | 69.5 | 69.9 | 69.5 | 68.5 | 66.8 | 64.4 | 61.3 | 57.5 | 53.0 |
| 0.042 | 63.5 | 65.9 | 67.7 | 68.8 | 69.1 | 68.8 | 67.8 | 66.2 | 63.8 | 60.7 | 57.0 | 52.6 |
| 0.044 | 62.6 | 65.1 | 66.9 | 68.0 | 68.4 | 68.2 | 67.2 | 65.6 | 63.2 | 60.2 | 56.5 | 52.2 |
| 0.046 | 61.7 | 64.3 | 66.1 | 67.3 | 67.7 | 67.5 | 66.6 | 65.0 | 62.7 | 59.8 | 56.1 | 51.8 |
| 0.048 | 60.9 | 63.5 | 65.4 | 66.6 | 67.1 | 66.9 | 66.0 | 64.5 | 62.2 | 59.3 | 55.7 | 51.4 |
| 0.050 | 60.1 | 62.7 | 64.6 | 65.9 | 66.4 | 66.3 | 65.5 | 64.0 | 61.8 | 58.9 | 55.3 | 51.1 |
| 0.052 | 59.3 | 62.0 | 63.9 | 65.2 | 65.8 | 65.7 | 65.0 | 63.5 | 61.4 | 58.5 | 55.0 | 50.8 |
| 0.054 | 58.5 | 61.3 | 63.3 | 64.6 | 65.2 | 65.2 | 64.5 | 63.1 | 60.9 | 58.2 | 54.7 | 50.5 |
| 0.056 | 57.8 | 60.6 | 62.6 | 64.0 | 64.7 | 64.7 | 64.0 | 62.6 | 60.6 | 57.8 | 54.4 | 50.3 |
| 0.058 | 57.1 | 59.9 | 62.0 | 63.4 | 64.2 | 64.2 | 63.6 | 62.2 | 60.2 | 57.5 | 54.1 | 50.0 |
| 0.060 | 56.4 | 59.3 | 61.4 | 62.9 | 63.7 | 63.8 | 63.2 | 61.9 | 59.9 | 57.2 | 53.9 | 49.9 |
| 0.062 | 55.8 | 58.7 | 60.9 | 62.4 | 63.2 | 63.3 | 62.8 | 61.5 | 59.6 | 57.0 | 53.7 | 49.7 |
| 0.064 | 55.2 | 58.1 | 60.3 | 61.9 | 62.7 | 62.9 | 62.4 | 61.2 | 59.3 | 56.8 | 53.5 | 49.5 |
| 0.066 | 54.6 | 57.5 | 59.8 | 61.4 | 62.3 | 62.5 | 62.1 | 60.9 | 59.1 | 56.6 | 53.3 | 49.4 |
| 0.068 | 54.0 | 57.0 | 59.3 | 61.0 | 61.9 | 62.2 | 61.8 | 60.7 | 58.9 | 56.4 | 53.2 | 49.4 |
| 0.070 | 53.5 | 56.5 | 58.9 | 60.6 | 61.6 | 61.9 | 61.5 | 60.4 | 58.7 | 56.2 | 53.1 | 49.3 |
| 0.072 | 53.0 | 56.1 | 58.5 | 60.2 | 61.2 | 61.6 | 61.3 | 60.2 | 58.5 | 56.1 | 53.0 | 49.3 |
| 0.074 | 52.5 | 55.6 | 58.1 | 59.8 | 60.9 | 61.3 | 61.0 | 60.1 | 58.4 | 56.0 | 53.0 | 49.3 |
| 0.076 | 52.0 | 55.2 | 57.7 | 59.5 | 60.6 | 61.1 | 60.8 | 59.9 | 58.3 | 56.0 | 53.0 | 49.3 |
| 0.078 | 51.6 | 54.8 | 57.4 | 59.2 | 60.4 | 60.9 | 60.7 | 59.8 | 58.2 | 55.9 | 53.0 | 49.3 |
| 0.080 | 51.2 | 54.5 | 57.0 | 58.9 | 60.2 | 60.7 | 60.5 | 59.7 | 58.1 | 55.9 | 53.0 | 49.4 |
| 0.082 | 50.8 | 54.1 | 56.8 | 58.7 | 60.0 | 60.5 | 60.4 | 59.6 | 58.1 | 55.9 | 53.1 | 49.5 |
| 0.084 | 50.4 | 53.8 | 56.5 | 58.5 | 59.8 | 60.4 | 60.3 | 59.6 | 58.1 | 56.0 | 53.2 | 49.7 |
| 0.086 | 50.1 | 53.5 | 56.3 | 58.3 | 59.6 | 60.3 | 60.3 | 59.6 | 58.2 | 56.1 | 53.3 | 49.8 |
| 0.088 | 49.8 | 53.3 | 56.0 | 58.1 | 59.5 | 60.2 | 60.2 | 59.6 | 58.2 | 56.2 | 53.4 | 50.0 |
| 0.090 | 49.6 | 53.1 | 55.9 | 58.0 | 59.4 | 60.2 | 60.2 | 59.6 | 58.3 | 56.3 | 53.6 | 50.2 |
| 0.092 | 49.3 | 52.9 | 55.7 | 57.9 | 59.4 | 60.1 | 60.3 | 59.7 | 58.4 | 56.4 | 53.8 | 50.5 |
| 0.094 | 49.1 | 52.7 | 55.6 | 57.8 | 59.3 | 60.2 | 60.3 | 59.8 | 58.5 | 56.6 | 54.0 | 50.7 |
| 0.096 | 48.9 | 52.5 | 55.5 | 57.7 | 59.3 | 60.2 | 60.4 | 59.9 | 58.7 | 56.8 | 54.3 | 51.0 |
| 0.098 | 48.8 | 52.4 | 55.4 | 57.7 | 59.3 | 60.2 | 60.5 | 60.0 | 58.9 | 57.1 | 54.6 | 51.4 |
| 0.100 | 48.6 | 52.3 | 55.4 | 57.7 | 59.4 | 60.3 | 60.6 | 60.2 | 59.1 | 57.3 | 54.9 | 51.7 |

Best Mode

The best mode presently contemplated for carrying out each of the three modes of the invention is summarized in Table 16.

Preferred embodiments of the invention are illustrated by the above descriptions and examples. However, the invention is not limited to the precise constructions herein disclosed but, rather, includes all modifications and changes coming within the scope of the following claims.

I claim:

1. Apparatus including:
A: an improved microfiltration module for separating whole blood into a cellular-enriched fraction and a plasma-enriched fraction, the module comprising in combination a bundle consisting of a plurality of blood wettable porous membrane hollow fibers all of which are in parallel bundle alignment and have pores of substantially uniform diameter and capable of passing plasma but not cellular components, each of the fibers having a pore diameter within the range 0.1 to 1.0 μm and a lumen diameter (D) no greater than 0.050 cm, the fibers being of substantially equal lengths and terminating in first open ends and second open ends; a liquid tight housing to contain the fibers; liquid tight sealing means cooperating with the housing and the first open ends of the fibers; liquid tight sealing means cooperating with the housing and the second open ends of the fibers, the two sealing means dividing the housing into two end chambers and one central chamber, the end chambers being in liquid transfer relationship with each other through the hollow fibers; blood inlet means for introducing whole blood into one chamber; blood outlet means for removing a cellular-enriched blood fraction from the other end chamber; and plasma outlet means for removing a plasma-enriched blood fraction from the central chamber, the improvement characterized in that the effective length (L), that is, the portion of each fiber, between the ends, through which plasma passes, to lumen diameter (D) ratio (L/D) is not greater than 16,400 cm$^{-1}$ D (L and D being in centimeters); and B. means, operably associated with the microfiltration module, for conducting blood through the fibers in reciprocatory pulsatile flow.

2. Apparatus of claim 1 wherein the L/D ratio is not greater than about 540.

3. Apparatus of claim 1 wherein the L/D ratio is about 100 to about 350.

4. Apparatus of claim 3 wherein the pore diameter is within the range 0.4 to 0.6 μm and the lumem diameter is 0.015 to 0.050 cm.

5. Apparatus of claim 1 wherein the fibers are blood wettable polypropylene fibers.

6. Apparatus of claim 1 wherein the fibers are purged of air and filled with saline.

7. Apparatus of claim 1 wherein the means for conducting blood through the fibers in reciprocatory pulsatile flow comprises a blood circulating loop between an inlet and an outlet, there being an oscillator located on the loop.

* * * * *